(12) United States Patent
Sandanayaka et al.

(10) Patent No.: US 7,728,032 B2
(45) Date of Patent: Jun. 1, 2010

(54) PHENOXYMETHYLALKYNE INHIBITORS OF LTA4H FOR TREATING INFLAMMATION

(75) Inventors: Vincent Sandanayaka, Northboro, MA (US); Pushpa Chandrasekar, Irvine, CA (US); Mark E. Gurney, Grand Rapids, MI (US)

(73) Assignee: deCODE genetics ehf (IS)

( * ) Notice: Subject to any disclaimer, the term of this patent is extended or adjusted under 35 U.S.C. 154(b) by 179 days.

(21) Appl. No.: 11/832,816

(22) Filed: Aug. 2, 2007

(65) Prior Publication Data

US 2008/0090839 A1    Apr. 17, 2008

Related U.S. Application Data

(60) Provisional application No. 60/821,482, filed on Aug. 4, 2006.

(51) Int. Cl.
| | |
|---|---|
| A01N 43/36 | (2006.01) |
| C07D 145/151 | (2006.01) |
| C07D 207/00 | (2006.01) |
| C07D 207/04 | (2006.01) |
| C07D 207/46 | (2006.01) |
| C07D 295/00 | (2006.01) |

(52) U.S. Cl. .................. 514/423; 514/428; 548/531; 548/570

(58) Field of Classification Search ............. 514/423, 514/428; 548/531, 570
See application file for complete search history.

(56) References Cited

U.S. PATENT DOCUMENTS

| | | | | |
|---|---|---|---|---|
| 3,838,162 | A * | 9/1974 | Maier et al. | ............ 548/247 |
| 5,324,718 | A | 6/1994 | Loftsson | |
| 5,472,954 | A | 12/1995 | Loftsson | |
| 2002/0013341 | A1 | 1/2002 | Duan et al. | |
| 2005/0043378 | A1 | 2/2005 | Axe et al. | |
| 2005/0043379 | A1 | 2/2005 | Axe et al. | |

FOREIGN PATENT DOCUMENTS

| | | |
|---|---|---|
| DE | 2129803 A1 | 12/1972 |
| WO | WO 96/41625 A | 12/1996 |
| WO | WO 98/40364 A | 9/1998 |
| WO | WO 00/44709 A | 8/2000 |
| WO | WO 00/44723 A | 8/2000 |
| WO | WO 01/55112 A | 8/2001 |
| WO | WO 02/076440 A | 10/2002 |
| WO | WO 2005/095387 A | 10/2005 |

OTHER PUBLICATIONS

Zask, A., et al: "Synthesis and SAR of diazepine and thiazepine TACE and MMP inhibitors", Bioorganic & Medicinal Chemistry Letters, Mar. 15, 2005, pp. 1641-1645, vol. 15, No. 9.

Inverarity, Iain A. and Hulme, Alison N: "Marked small molecule libraries: a truncated approach to molecular probe design," Organic & Biomolecular Chemistry, Feb. 21, 2007, pp. 636-643, vol. 5, No. 4.

International Search Report and the Written Opinion of the International Searching Authority, corresponding to PCT/US2007/075051.

Remenar, Julius F., et al., "Crystal Engineering of Novel Cocrystals of a Triazole Drug with 1,4-Dicarboxylic Acids", Journal of American Chemical Society, vol. 125, No. 28 (2003), pp. 8456-8457.

Kachur, James F., et al., "Pharmacological Characterization of SC-57461A (3-[Methyl[3-[4-(phenylmethyl)phenoxy]propyl]amino]propanoic Acid HCI), a Potent and Selective Inhibitor of Leukotriene A4 Hydrolase I: In Vitro Studies", The Journal of Pharmacology and Experimental Therapeutics, vol. 300, NO. 2 (Feb. 2002), pp. 577-582.

Mueller, Martin J., et al., "Leukotriene A4 Hydrolase, Mutation of Tyrosine 378 Allows Conversion of Leukotriene A4 into an Isomer of Leukotriene B4", The Journal of Biological Chemistry, vol. 271, No. 40 (Oct. 4, 1996), pp. 24345-24348.

Helgadottir, Anna, et al., "The gene encoding 5-lipoxygenase activating protein confers risk of myocardial infarction and stroke", Nature Genetics, vol. 36, No. 3 (Mar. 2004), doi: 10.1038/ng1311, pp. 233-239.

Maehr, Hubert, "A proposed new convention for graphic presentation of molecular geometry and topography", Journal of Chemical Education, vol. 62 (1985), pp. 114-120.

Penning, T.D., "Inhibitors of Leukotriene A4 (LTA4) Hydrolase as Potential Anti Inflammatory Agents", Current Pharmaceutical Design, vol. 7, No. 3 (Feb. 1, 2001), doi 10.2174/1381612013398248, pp. 163-179.

* cited by examiner

*Primary Examiner*—James O Wilson
*Assistant Examiner*—Erich A Leeser
(74) *Attorney, Agent, or Firm*—Heslin Rothenberg Farley & Mesiti P.C.

(57) ABSTRACT

A chemical genus of biphenyl heterocycle derivative inhibitors of LTA4H (leukotriene A4 hydrolase) of the formula:

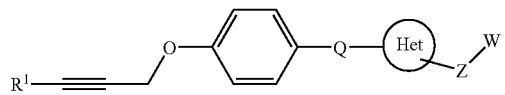

is disclosed. In these compounds Q and Z are $(CH_2)_{1-10}$; in which one or two $(CH_2)$ may optionally be replaced by —O—, —$NR^1$—, —SO—, —$S(O)_2$—, —C(=O)— or —C=O(NH)—; Het is a 5-7 membered non-aromatic nitrogen heterocycle; and W is acyl, hydroxyl, carboxyl, amino, carboxamido, aminoacyl, —COOalkyl, —CHO, heterocyclyl, substituted aryl, or substituted heterocyclyl, or taken together ZW can be H or —COOalkyl. The compounds are useful for the treatment and prevention and prophylaxis of inflammatory diseases and disorders.

5 Claims, No Drawings

PHENOXYMETHYLALKYNE INHIBITORS OF LTA4H FOR TREATING INFLAMMATION

RELATED APPLICATIONS

This application claims priority to U.S. Provisional Application No. 60/821,482 filed Aug. 4, 2006, which is hereby incorporated herein by reference in its entirety.

FIELD OF THE INVENTION

The present invention relates to a chemical genus of biphenyl heterocycle derivative inhibitors of LTA4H (leukotriene A4 hydrolase) useful for the treatment and prevention and prophylaxis of inflammatory diseases and disorders.

BACKGROUND OF THE INVENTION

The end products of the leukotriene pathway are potent inflammatory lipid mediators derived from arachidonic acid. They can potentially contribute to development of atherosclerosis and destabilization of atherosclerotic plaques through lipid oxidation and/or proinflammatory effects. As described elsewhere, a gene on chromosome 13q12 has been identified as playing a major role in myocardial infarction (MI), [Helgadottir et al., *Nature Genetics* doi: 10.1038/ng 1311, 8 Feb. 2004]. This gene (ALOX5AP), herein after referred to as an MI disease gene, comprises nucleic acid that encodes 5-lipoxygenase activating protein (FLAP), herein after referred to as FLAP. DNA variants in the FLAP gene increase risk for myocardial infarction by 1.8 fold and for stroke by 1.7 fold. The leukotriene pathway, through FLAP, leads to the production of leukotriene B4 by the enzyme leukotriene A4 hydrolase (LTA4H). Leukotriene B4 is one of the most potent chemokine mediators of arterial inflammation. Particular DNA variants in the gene encoding LTA4H also elevate risk for MI and stroke, as described elsewhere [Hakonarsson et al., *J. Am. Med. Assoc.* 293, 2245-2256 (2005)]. Individuals with a prior history of MI produce more leukotriene B4 when their isolated neutrophils are stimulated with ionomycin. Increased LTB4 production is particularly marked in male patients with a prior history of MI who carry risk variants in the FLAP gene [Helgadottir et al.]. The treatment (prophylactic and/or therapeutic) of certain diseases and conditions (e.g., MI, acute coronary syndrome (ACS), stroke, atherosclerosis) associated with FLAP or with LTA4H can be accomplished by inhibiting LTA4H. Inhibiting LTA4H is advantageous for methods of treatment for MI or susceptibility to MI; for ACS (e.g., unstable angina, non-ST-elevation myocardial infarction (NSTEMI) or ST-elevation myocardial infarction (STEMI)); for decreasing risk of a second MI; for stroke (including transient ischemic attack) or susceptibility to stroke; for atherosclerosis, such as for patients requiring treatment (e.g., angioplasty, stents, coronary artery bypass graft) to restore blood flow in coronary arteries, such as patients requiring treatment for peripheral vascular disease including peripheral occlusive arterial disease, critical limb ischemia (e.g., gangrene, ulceration), and intermittent claudication to restore blood flow in the lower limbs; for atherosclerotic reno-vascular disease; for abdominal aortic aneurysm; and/or for decreasing leukotriene synthesis (e.g., for treatment of MI).

US Patent Application Publication No. 20050043378 and 20050043379, relate to benzooxazol-2-yl, benzothiazol-2-yl and 1H-benzoimidazol-2-yl compounds and derivatives thereof useful as leukotriene A4 hydrolase (LTA4H) inhibitors in treating inflammation and disorders associated with inflammation. These disclosures are incorporated herein by reference as they relate to utility.

SUMMARY OF THE INVENTION

The present invention relates to compounds exhibiting LTA4H enzyme inhibition, having general formula:

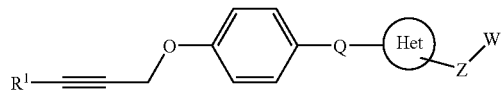

wherein $R^1$ is selected from the group consisting of H, alkyl, aryl, heteroaryl, aryl substituted with from one to three substituents independently selected from the group consisting of halogen, loweralkyl, loweracyl, loweralkoxy, fluoroloweralkyl, fluoroloweralkoxy, hydroxyloweralkyl, formyl, cyano, benzyl, benzyloxy, phenyl, heteroaryl, heterocyclylalkyl and nitro; and heteroaryl substituted with from one to three substituents independently selected from the group consisting of halogen, loweralkyl, loweracyl, loweralkoxy, fluoroloweralkyl, fluoroloweralkoxy, formyl, cyano, phenyl, heteroaryl, heterocyclylalkyl and nitro;

Q is $(CH_2)_{1-8}$; in which one or two $(CH_2)$ may optionally be replaced by —O—, —$NR^1$—, —SO—, —$S(O)_2$—, —C(=O)— or —C=O(NH)—, provided that said —O—, —$NR^1$—, —SO—, —$S(O)_2$—, —C(=O)— or —C=O (NH)— are separated by at least one —$(CH_2)$—; and when Het is a nitrogen-attached heterocycle, Q may additionally be a direct bond;

Het is a 5-7 membered non-aromatic nitrogen heterocycle;

Z is $(CH_2)_{1-10}$; in which one or two $(CH_2)$ may optionally be replaced by —O—, —$NR^1$—, —SO—, —$S(O)_2$—, —C(=O)— or —C=O(NH)—, provided that said —O—, —$NR^1$—, —SO—, —$S(O)_2$—, —C(=O)— or —C=O (NH)— are not at the point of attachment to nitrogen and are separated by at least one —$(CH_2)$—;

W is selected from acyl, hydroxyl, carboxyl, amino, carboxamido, aminoacyl, —COOalkyl, —CHO, sulfonamide, —C(O)fluoroalkyl, —C(O)CH$_2$C(O)Oalkyl, —C(O)CH$_2$C(O)Ofluoroalkyl, —SH, —C(O)NH(OH), —C(O)N(OH)$R^4$, —N(OH)C(O)OH, —N(OH)C(O)$R^4$, heterocyclyl, substituted aryl, and substituted heterocyclyl, or taken together ZW are H or —COOalkyl; and $R^4$ is selected from the group consisting of H and lower alkyl.

In a second aspect the invention relates to pharmaceutical compositions comprising a pharmaceutically acceptable carrier and a therapeutically effective amount of at least one of the compounds as described herein.

In a third aspect, the invention relates to methods for the treatment and prevention or prophylaxis of a disease, condition or disorder associated with leukotriene A4 hydrolase. The methods comprise administering to a mammal a therapeutically effective amount of a compound described above. The disease or condition may be related to allergic, acute or chronic inflammation. The disease may be for example contact and atopic dermatitis, arthritis, allergic rhinitis, asthma or an autoimmune diseases such as Crohn's disease, psoriasis, ulcerative colitis, inflammatory bowel disease, multiple sclerosis, ankylosing spondylitis, and the like. Similarly, the compounds defined above can be used in preventing recurring inflammatory attacks. The compounds are also useful for treating and preventing atherosclerosis, thrombosis, stroke, acute coronary syndrome, stable angina, peripheral vascular disease, critical leg ischemia, intermittent claudication, abdominal aortic aneurysm and myocardial infarction.

DETAILED DESCRIPTION OF THE INVENTION

Throughout this specification the substituents are defined when introduced and retain their definitions.

In one aspect the invention relates to heterocycle derivatives useful as LTA4H enzyme inhibitors, having the general formula:

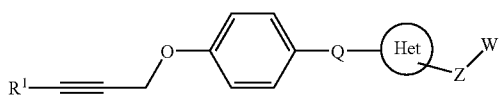

In some embodiments the compounds have the formula

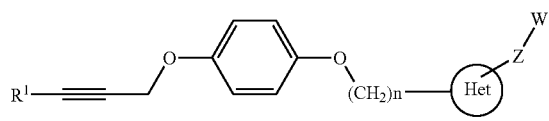

wherein n is 1-4 and Het is chosen from pyrrolidine, piperidine and piperazine.

In other embodiments, Q is a direct bond and Het is a piperazine. These compounds have the formula

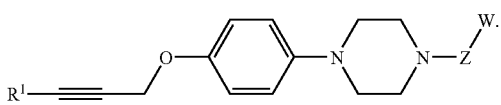

In many embodiments Z is $(CH_2)_{1-5}$ and W is COOH. In many other embodiments, $R^1$ is H, methyl, phenyl or substituted phenyl.

In another aspect the present invention provides pharmaceutical compositions comprising a pharmaceutically acceptable carrier and a therapeutically effective amount of at least one compound as described above.

Methods of the invention parallel the compositions and formulations. The methods comprise administering to a patient in need of treatment a therapeutically effective amount of a compound according to the invention.

The present invention provides a method for inhibiting leukotriene A4 hydrolase comprising contacting the LTA4H enzyme with a therapeutically effective amount of a compound according to the general formula.

Furthermore, the present invention provides a method for treating a disorder associated with leukotriene A4 hydrolase comprising administering to a mammal a therapeutically effective amount of a compound or a salt, hydrate or ester thereof according to the general formula given above. It may be found upon examination that additional species and genera not presently excluded are not patentable to the inventors in this application. In either case, the exclusion of species and genera in applicants' claims are to be considered artifacts of patent prosecution and not reflective of the inventors' concept or description of their invention. The invention, in a composition aspect, is all compounds of the general formula above, except those that are in the public's possession. The invention, in a method aspect, is a method employing compounds of the general formula above, except those methods that are in the public's possession.

In some embodiments the disorder is associated with inflammation. In some embodiments the disorder is selected from allergic inflammation, acute inflammation and chronic inflammation.

Compounds of the genus represented by the general formula above are inhibitors of $LTA_4H$ enzyme. As such they have utility in treating and preventing inflammatory diseases and disorders, as described above, particularly for such conditions as asthma, chronic obstructed pulmonary disease (COPD), atherosclerosis, rheumatoid arthritis, multiple sclerosis, inflammatory bowel diseases (IBD)—including Crohn's disease and ulcerative colitis—or psoriasis, which are each characterized by excessive or prolonged inflammation at some stage of the disease.

Recent research indicates that the compounds are also useful for treating and preventing atherosclerosis, thrombosis, stroke, acute coronary syndrome, stable angina, peripheral vascular disease, critical leg ischemia, intermittent claudication, abdominal aortic aneurysm and myocardial infarction.

The compounds may be presented as salts. The term "pharmaceutically acceptable salt" refers to salts whose counter ion derives from pharmaceutically acceptable non-toxic acids and bases. Suitable pharmaceutically acceptable base addition salts for the compounds of the present invention include, but are not limited to, metallic salts made from aluminum, calcium, lithium, magnesium, potassium, sodium and zinc or organic salts made from lysine, N,N-dialkyl amino acid derivatives (e.g. N,N-dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine) and procaine. When the compounds contain a basic residue, suitable pharmaceutically acceptable base addition salts for the compounds of the present invention include inorganic acids and organic acids. Examples include acetate, benzenesulfonate (besylate), benzoate, bicarbonate, bisulfate, carbonate, camphorsulfonate, citrate, ethanesulfonate, fumarate, gluconate, glutamate, bromide, chloride, isethionate, lactate, maleate, malate, mandelate, methanesulfonate, mucate, nitrate, pamoate, pantothenate, phosphate, succinate, sulfate, tartrate, p-toluenesulfonate, and the like.

For convenience and clarity certain terms employed in the specification, examples and claims are described herein.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, alkenyl, alkynyl, aryl, arylalkyl and combinations thereof. Examples include phenethyl, cyclohexylmethyl, camphoryl, adamantyl and naphthylethyl.

Alkoxy or alkoxyl refers to groups of from 1 to 8 carbon atoms of a straight, branched, cyclic configuration and combinations thereof attached to the parent structure through oxygen. Examples include methoxy, ethoxy, propoxy, isopropoxy, cyclopropyloxy, cyclohexyloxy and the like. Loweralkoxy refers to groups containing one to four carbons.

Alkoxyalkyl refers to ether groups of from 3 to 8 atoms of a straight, branched, cyclic configuration and combinations thereof attached to the parent structure through an alkyl. Examples include methoxymethyl, methoxyethyl, ethoxypropyl, and the like.

Alkoxyaryl refers to alkoxy substituents attached to an aryl, wherein the aryl is attached to the parent structure. Arylalkoxy refers to aryl substituents attached to an oxygen, wherein the oxygen is attached to the parent structure. Substituted arylalkoxy refers to a substituted aryl substituent attached to an oxygen, wherein the oxygen is attached to the parent structure.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene and naphthalene, and according to the invention benzoxalane and residues in which one or more rings are aromatic, but not all need be. The 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. Examples include, e.g., pyridinylmethyl, pyrimidinylethyl and the like. Heterocyclylalkyl refers to a substituent in which a heterocyclyl residue is attached to the parent structure through alkyl. Examples include morpholinoethyl and pyrrolidinylmethyl.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulphurs, as well as other heteroatoms. A nitrogen heterocycle is a heterocycle containing at least one nitrogen in the ring; it may contain additional nitrogens, as well as other heteroatoms. Oxygen heteroaryl is a subset of oxygen heterocycle; examples include furan and oxazole. Sulphur heteroaryl is a subset of sulphur heterocycle; examples include thiophene and thiazine. Nitrogen heteroaryl is a subset of nitrogen heterocycle; examples include pyrrole, pyridine and pyrazine. A saturated nitrogenous heterocycle is a subset of nitrogen heterocycle. Saturated nitrogenous heterocycle contain at least one nitrogen and may contain additional nitrogens, as well as other heteroatoms. Examples include pyrrolidine, pyrazolidine, piperidine, morpholine, and thiomorpholine.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The terms "halogen" and "halo" refer to fluorine, chlorine, bromine or iodine.

The term "prodrug" refers to a compound that is made more active in vivo. Activation in vivo may come about by chemical action or through the intermediacy of enzymes. Microflora in the GI tract may also contribute to activation in vivo.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Radiolabeled compounds of formula of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

As used herein, and as would be understood by the person of skill in the art, the recitation of "a compound" is intended to include salts, solvates, co-crystals and inclusion complexes of that compound.

The term "solvate" refers to a compound of formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Co-crystals are combinations of two or more distinct molecules arranged to create a unique crystal form whose physical properties are different from those of its pure constituents. Pharmaceutical co-crystals have recently become of considerable interest for improving the solubility, formulation and bioavailability of such drugs as itraconazole [see Remenar et al. J. Am. Chem. Soc. 125, 8456-8457 (2003)] and fluoxetine. Inclusion complexes are described in Remington: The Science and Practice of Pharmacy 19$^{th}$ Ed. (1995) volume 1, page 176-177. The most commonly employed inclusion complexes are those with cyclodextrins, and all cyclodextrin complexes, natural and synthetic, with or without added additives and polymer(s), as described in U.S. Pat. Nos. 5,324,718 and 5,472,954, are specifically encompassed within the claims. The disclosures of Remington and the '718 and '954 patents are incorporated herein by reference.

[The compounds described herein may contain asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-isomers may be prepared using chiral synthons or chiral reagents, or resolved using conventional techniques. The prefix "rac" refers to a racemate. When the compounds described herein contain olefinic double bonds or other centers of geometric asymmetry, and unless specified otherwise, it is intended that the compounds include both E and Z geometric isomers. The representation of the configuration of any carbon-carbon double bond appearing herein is selected for convenience only, and unless explicitly stated, is not intended to designate a particular configuration. Thus a carbon-carbon double bond depicted arbitrarily as E may be Z, E, or a mixture of the two in any proportion. Likewise, all tautomeric forms are also intended to be included.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group, which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the Journal of Organic Chemistry. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures.

EXAMPLES

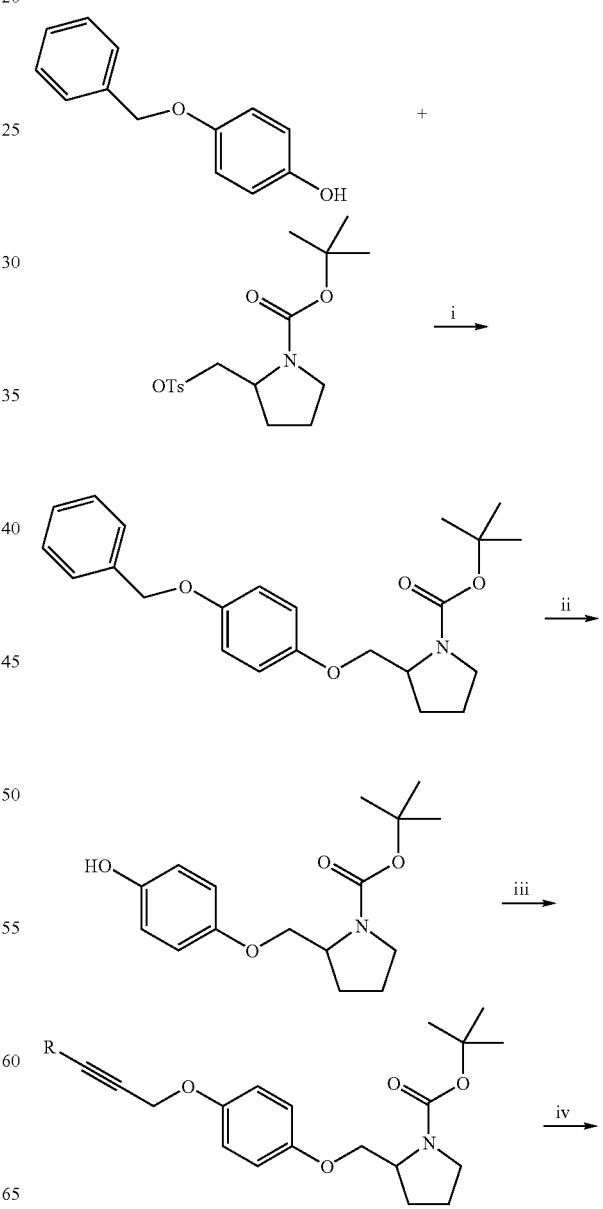

-continued

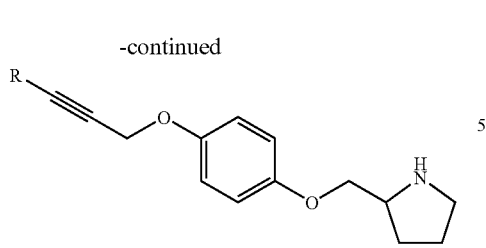

Scheme I: (i) NaH, DMF; (ii) H2, Pd/C; (iii) R-substituted propargyl bromide, K2CO3; (iv) 2M HCl, ether.

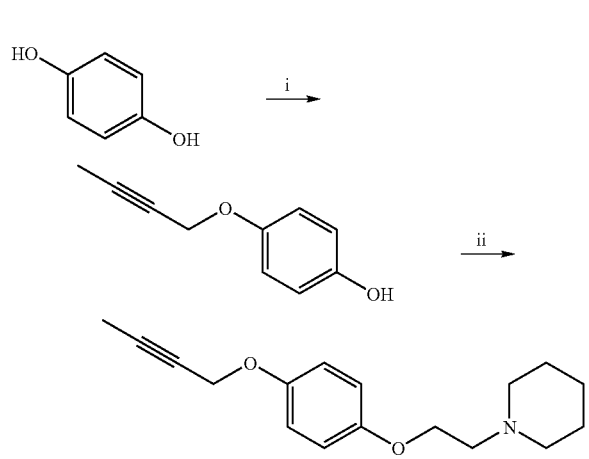

Scheme II: (i) butnyl bromide, K2CO3 (ii) piperidine ethyl chloride, K2CO3

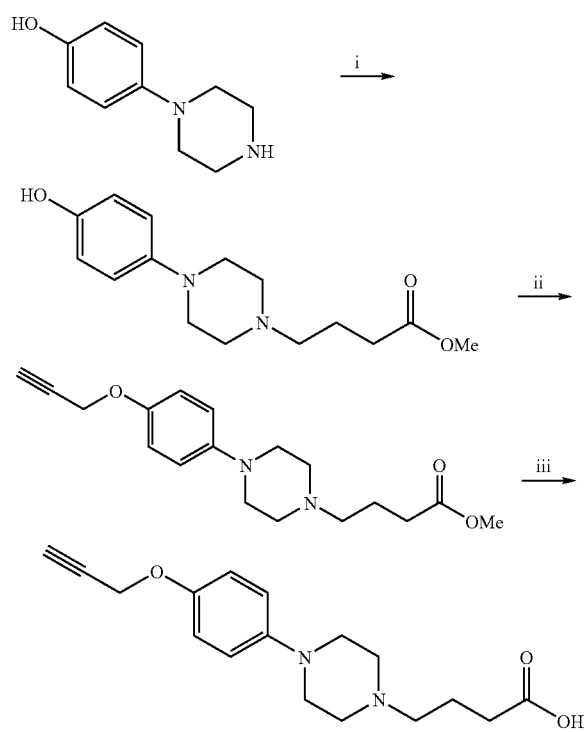

Scheme III: (i) methyl bromobutyrate, Et3N (ii) 3-bromopropyne, K2CO3 (iii) 1N NaOH Example 1

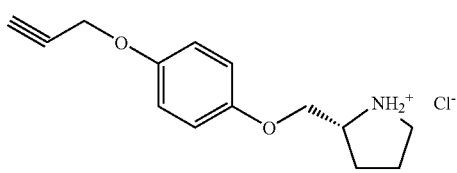

Step 1

2-(4-Benzyloxy-phenoxymethyl)-pyrrolidine-1-carboxylic acid tert-butyl ester

To a 15 mL of anhydrous DMF was added NaH (60% dispersion in oil, 338 mg, 8.44 mmol), and the resulting reaction mixture was cooled to 0° C. p-benzyloxy phenol (1.41 g, 7.03 mmol) was added and the reaction mixture was stirred at rt for 45 min. It was then cooled to −5° C., and (R)-Boc-prolinol tosylate (2.5 g, 7.03 mmol) in anhydrous DMF (5 mL) was cooled in a separate ice-bath and added dropwise to the reaction mixture. It was then allowed to warm to rt and stirred at 92° C. for 5 h and at rt overnight. The resulting mixture was poured into 200 mL ice/water and stirred for an hour. The resulting precipitate was filtered, washed with ether, dried over MgSO$_4$, concentrated, recrystallized with ether/hexane to give shiny yellow crystals (1.5 g, 55%).

Step 2

2-(4-Hydroxy-phenoxymethyl)-pyrrolidine-1-carboxylic acid tert-butyl ester

A solution of the product from step 1, in THF (11 ml), EtOH (25 ml), Pd—C (1.17 g, 10% wt) in a round bottom flask was charged with H$_2$-balloon after flushing with hydrogen 3 times. The resulting solution was stirred overnight at rt. The reaction mixture was then filtered, washed with THF (30 ml), EtOH (25 ml) and dried over anhydrous MgSO$_4$. After removal of the solvent in vacuo, the product was obtained as an orange oil (1.0 g, 95%).

Step 3

2-(4-Prop-2-ynyloxy-phenoxymethyl)-pyrrolidine-1-carboxylic acid tert-butyl ester To a solution of the product from step 2 (2.0 g, 6.82 mmol) in anhydrous DMF (50 mL) was added dry K$_2$CO$_3$ (4.6 g, 33 mmol) and allowed to stir for 15 min. Propargyl bromide (1.214 g, 10.20 mmol) in anhydrous DMF (10 mL) was added and the reaction mixture stirred at 50° C. for 6 h, then at rt for 48 h. The reaction mixture was concentrated, taken up in EtOAc, washed with water, dried over anhydrous MgSO$_4$ and the solvent removed in vacuo. The product was purified by silica gel flash chromatography using EtOAc/hexane to obtain the title compound (2.0 g, 88%).

Step 4

(R)-2-(4-Prop-2-ynyloxy-phenoxymethyl)-pyrrolidine hydrochloride

To a solution of the product from step 3 (100 mg) was added 2M HCl in dioxane (4 mL) and the resulting mixture was stirred for 2 h, and the solvent was removed in vacuo. Crude material was triturated with ether to obtain the title product (70 mg, 100%); LCMS; 97%, m/z 232.1 (M+1); $^1$H NMR (DMSO-$d_6$, 400 MHz) δ 1.70 (1H, m), 1.95 (2H, m), 2.10 (2H, m), 3.20 (2H, m), 3.53 (2H, m), 3.86 (1H, m), 4.07 (1H, dd, J1=8.0 Hz, J2=10.0 Hz), 4.18 (1H, dd, J1=4.0 Hz, J2=10.8 Hz), 6.94 (4H, s), 9.2 (2H, br s).

General Procedures for Examples 2-4

A: PdCl$_2$ (0.02 equiv), aryl iodide (1.0 equiv), H$_2$O (0.07 equiv), and pyrrolidine (5 equiv) were added to a flask under aerobic conditions, and the resulting mixture was stirred at 50° C. for 5 min. To this solution was added 2-(4-prop-2-ynyloxy-phenoxymethyl)-pyrrolidine-1-carboxylic acid tert-butyl ester (1.2 equiv) and the reaction mixture was stirred at 50° C. for 24 h. The reaction mixture was then extracted with EtOAc and the combined organic layer was dried over anhydrous MgSO$_4$. The solvent was removed under vacuum, and the residue was purified by flash chromatography.

B: The product from General Procedure A was dissolved in 4.0M HCl in dioxane (excess) the resulting mixture stirred for 2 h at rt. The solvent was removed in vacuo to obtain a thick oil. The oil was triturated with ether to obtain the product as the HCl salt.

Example 2

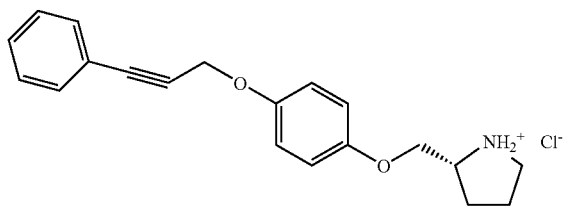

Step 1

2-[4-(3-Phenyl-prop-2-ynyloxy)-phenoxymethyl]-pyrrolidine-1-carboxylic acid tert-butyl ester General procedure A was followed using the product from step 3, Example 1 (165 mg, 0.498 mmol), iodobenzene (85 mg, 0.416 mmol), PdCl$_2$ (2.5 mg, 0.014 mmol), pyrrolidine (0.2 mL, 2.37 mmol), water (0.53 mL) to give the title compound (30 mg, 15%).

Step 2

2-[4-(3-Phenyl-prop-2-ynyloxy)-phenoxymethyl]-pyrrolidine

General procedure B was followed using the product from step 1, Example 2 (30 mg, 0.074 mmol) to give the title compound (13 mg, 51%); MS; m/z 308 (M+H) 99%; $^1$H NMR (DMSO, 400 MHz) δ 1.68-2.12 (4H, m), 3.19 (2H, m), 4.98 (2H, s), 6.96 (2H, d, J=9.6 Hz), 7.01 (2H, d, J=5.2 Hz), 7.42 (4H, m), 6.96 (2H, d, J=9.6 Hz), 7.01 (2H, d, J=5.2 Hz), 7.42 (4H, m).

Example 3

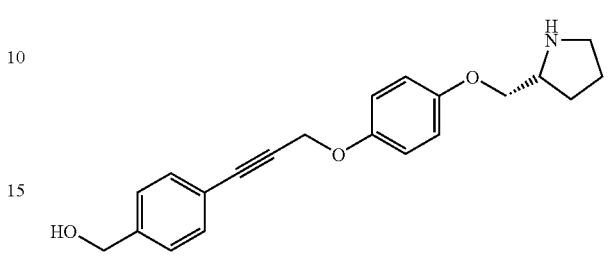

Step 1

2-{4-[3-(4-Hydroxymethyl-phenyl)-prop-2-ynyloxy]-phenoxymethyl}-pyrrolidine-1-carboxylic acid tert-butyl ester General procedure A was followed using the product from step 3 Example 1 (266 mg, 1.0546 mmol), p-iodobenzylalcohol (156.5 mg, 0.669 mmol), PdCl$_2$ (2.5 mg, 0.014 mmol), pyrrolidine (0.277 mL, 3.34 mmol), water (0.844 mL) to give the title compound (60 mg, 20.5%).

Step 2

(4-{3-[4-(Pyrrolidin-2-ylmethoxy)-phenoxy]-prop-1-ynyl}-phenyl)-methanol

General procedure B was followed using the product from step 1, Example 3 (100 mg, 0.21 mmol) to give the title compound (30 mg, 54%); MS m/z 338 (M+H)>95%; $^1$H NMR (DMSO-$d_6$, 400 MHz) δ 1.68-2.11 (4H, m), 3.20 (2H, m), 3.87 (1H, m), 4.20 (1H, dd, J=4.0 Hz, 10.8 Hz), 4.50 (2H, d, J=5.6 Hz), 4.97 (2H, s), 5.28 (OH, t, J=5.6 Hz), 6.96 (2H, d, J=9.2 Hz), 7.01 (2H, d, J=6.4 Hz), 7.32 (2H, d, J=8.8 Hz), 7.38 (2H, d, J=8.0 Hz).

Example 4

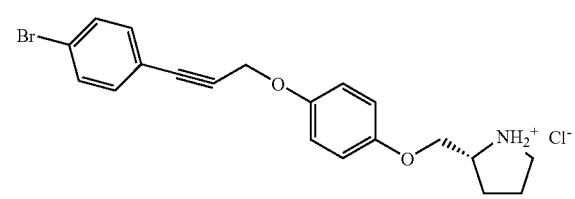

Step 1

2-{4-[3-(4-Bromo-phenyl)-prop-2-ynyloxy]-phenoxymethyl}-pyrrolidine-1-carboxylic acid tert-butyl ester General procedure A was followed using the product from step 3 Example 1 (266 mg, 0.803 mmol), p-bromo iodobenzene (156.5 mg, 0.669 mmol), PdCl$_2$ (2.5 mg, 0.014 mmol), pyrrolidine (0.277 mL, 3.34 mmol), water (0.844 mL) to give the title compound (110 mg, 33.8%).

Step 2

2-{4-[3-(4-Bromo-phenyl)-prop-2-ynyloxy]-phenoxymethyl}-pyrrolidine hydrochloride General procedure B was followed using the product from step 1, Example 4 (100 mg, 0.21 mmol) to give the title compound. (92 mg, 96%); MS m/z 423 (M+H) 99%: $^1$H NMR (DMSO, 400 MHz) δ 1.68-2.13 (4H, m), 3.20 (2H, m), 3.85 (1H, m), 4.06 (1H, dd, J=4.0 Hz, 10.8 Hz), 4.20 (1H, dd, J=104 Hz, 3.6 Hz), 4.97 (2H, s), 6.95 (2H, d, J=8.8 Hz), 7.01 (2H, d, J=9.2 Hz), 7.37 (2H, d, J=8.4 Hz), 7.59 (2H, d, J=8.4 Hz).

Example 5

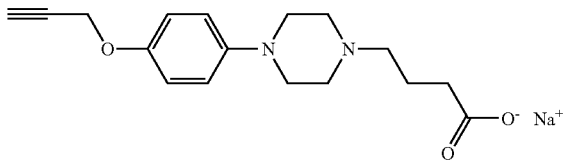

Step 1

3-[4-(4-Hydroxy-phenyl)-piperazin-1-yl]-butyric acid methyl ester

To a mixture of 4-piperazin-1-yl-phenol (2 g, 11.2 mmol) and methyl 3-bromo-butyrate (2.03 g, 11.2 mmol) in DMF (5 mL) was added triethylamine (4.5 mL, 11.53 mmol) dropwise and the reaction mixture was stirred at ambient temperature overnight. The mixture was poured onto water and extracted with ethyl acetate (50 ml×3). The combined organic layers were washed with brine, dried over anhydrous Na$_2$SO$_4$ and evaporated under vacuum to dryness. The residue was purified by silica gel flash chromatography (1% methanol in CH$_2$Cl$_2$) to furnish the title compound (1.85 g, 59.3%); MS; m/z 279 (M+H).

Step 2

3-[4-(4-Prop-2-ynyloxy-phenyl)-piperazin-1-yl]-propionic acid methyl ester

To a mixture of the compound from step 1 (278 mg, 1.0 mmol) and K$_2$CO$_3$ (152 mg, 1.1 mmol) in DMF (5 mL) was added 3-bromopropyne (130 mg, 1.1 mmol) dropwise at rt. The reaction mixture was stirred at rt overnight and then partitioned between water and ethyl acetate. The organic payers were combined and washed with brine, dried over anhydrous Na$_2$SO$_4$ and evaporated under vacuum to give a brown oil. The crude product was purified by silica gel flash chromatography (30% ethyl acetate in hexane) to furnish the title compound (120 mg, 38%) as a light yellow solid; MS; m/z 317 (M+H).

Step 3

3-[4-(4-Prop-2-ynyloxy-phenyl)-piperazin-1-yl]-propionic acid sodium salt

The compound from step 2 (175 mg, 0.55 mmol) was dissolved in methanol (4 mL) followed by addition of 1N NaOH aqueous solution (0.55 ml, 0.55 mmol). The reaction solution was stirred at 60-70° C. for 4 h and then evaporated under vacuum to dryness. The residue was stirred with ethyl acetate (4 mL) and the solid was collected by filtration and washed with ethyl acetate to give the title product as an off-white solid (75 mg, 42%); MS; m/z 289 (M+H).

Example 6

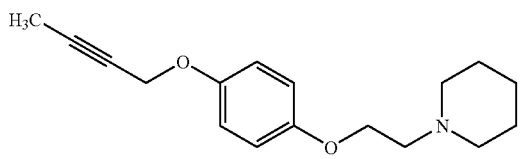

Step 1

4-But-2-ynyloxy-phenol

To a solution containing butynyl bromide (1 g, 7.5 mmol), hydroquinone (827 mg, 7.5 mmol), and K2CO3 (1.04 g, 7.5 mmol) was refluxed for 10 h. Solvent was removed in vacuo and the crude product was dissolved in EtOAc and partitioned with water. Organic layer was separated and washed with water and dried over anhydrous Na2SO4. The solvent was removed in vacuo to obtain the crude product (0.3 g, 25%), which was used for the next step without further purification; LCMS 99%, m/z 162.2 (M$^+$).

Step 2

1-[2-(4-But-2-ynyloxy-phenoxy)-ethyl]-piperidine

To a solution of the product from step 1 (200 mg, 1.23 mmol) in MeOH (10 mL) was added piperidine ethyl chloride hydrochloride (227 mg, 1.23 mmol), and K2CO3 (679 mg, 4.92 mmol), and the resulting mixture was refluxed for 10 h. Solvent was removed in vacuo and the crude product was dissolved in EtOAc and partitioned with water. Organic layer was separated and dried over anhydroua Na2SO4. Solvent was removed in vacuo to obtain a thick oil, which was added 2M HCl in ether. Solvent was decanted and the solid was triturated with ether to obtain the title product (100 mg, 30%); MS m/z 274.4 (M+H) 99%: $^1$H NMR (DMSO-d$_6$, 400 MHz) δ 1.39 (1H, m), 1.67-1.82 (8H, m), 2.97 (2H, m), 3.41-3.50 (1H, m), 3.75 (1H, br m), 4.31 (2H, d, J=5.2 Hz), 4.67 (2H, s).

In these reactions, it is also possible to make use of variants that are in themselves known, but are not mentioned here. The starting materials are either commercially available, synthesized as described in the examples or may be obtained by the methods well known to persons of skill in the art.

LTA4H inhibitors have been shown to be effective anti-inflammatory agents in pre-clinical studies. For example, oral administration of LTA4H inhibitor SC57461 to rodents resulted in the inhibition of ionophore-induced LTB4 production in mouse blood ex vivo, and in rat peritoneum in vivo (Kachur et al., 2002, J. Pharm. Exp. Ther. 300(2), 583-587). Furthermore, eight weeks of treatment with the same inhibitor compound significantly improved colitis symptoms in a primate model (Penning, 2001, Curr. Pharm. Des. 7(3): 163-179). The spontaneous colitis that develops in these animals is very similar to human IBD. Therefore persons of skill in the art accept that positive results in LTA4H models are predictive of therapeutic utility in this and other human inflammatory diseases.

The inflammatory response is characterized by pain, increased temperature, redness, swelling, or reduced function, or by a combination of two or more of these symptoms. The terms inflammation, inflammatory diseases or inflammation-mediated diseases or conditions include, but are not limited to, acute inflammation, allergic inflammation, and chronic inflammation.

Autoimmune diseases are associated with chronic inflammation. There are about 75 different autoimmune disorders known that may be classified into two types, organ-specific (directed mainly at one organ) and non-organ-specific (affecting multiple organs).

Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis.

Examples of non-organ-specific autoimmune disorders are rheumatoid arthritis, multiple sclerosis, systemic lupus and myasthenia gravis.

Furthermore, the compounds, compositions and methods of the present invention are useful in treating cancer. Leukotriene synthesis has been shown to be associated with different types of cancer including esophageal cancer, brain cancer, pancreatic cancer, and colon cancer.

The terms "methods of treating or preventing" mean amelioration, prevention or relief from the symptoms and/or effects associated with lipid disorders. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis. Throughout this application, various references are referred to. The disclosures of these publications in their entireties are hereby incorporated by reference as if written herein.

The term "mammal" is used in its dictionary sense. Humans are included in the group of mammals, and humans would be the preferred subjects of the methods of.

While it may be possible for the compounds of the formula above to be administered as the raw chemical, it is preferable to present them as a pharmaceutical composition. According to a further aspect, the present invention provides a pharmaceutical composition comprising a compound of formula shown above, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of the formula above or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder (including micronized and nanoparticulate powders) or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation. The dose range for adult humans is generally from 0.1 µg to 10 g/day orally. Tablets or other forms of presentation provided in discrete units may conveniently contain an amount of compound of the invention which is effective at such dosage or as a multiple of the same, for instance, units containing 0.1 mg to 500 mg, usually around 5 mg to 200 mg. The precise amount of compound administered to a patient will be the responsibility of the attendant physician. However, the dose employed will depend on a number of factors, including the age and sex of the patient, the precise disorder being treated, and its severity. The frequency of administration will depend on the pharmacodynamics of the individual compound and the formulation of the dosage form, which may be optimized by methods well known in the art (e.g. controlled or extended release tablets, enteric coating etc.).

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within any number of hours of each other or within any number or days or weeks of each other. In some cases even longer intervals are possible.

While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

As LTA4H inhibitors, the compounds of formula above have utility in treating and preventing inter alia inflammation. The compounds and compositions can be used advantageously in combination with other agents useful in treating and preventing inflammatory conditions and for treating and preventing atherosclerosis, thrombosis, stroke, acute coronary syndrome, stable angina, peripheral vascular disease, critical leg ischemia, intermittent claudication, abdominal aortic aneurysm and myocardial infarction.

Assays to Determine Potency of LTA$_4$ Hydrolase Inhibitors (1) In vitro assay testing inhibitory activity against purified recombinant human LTA$_4$ hydroase:

A human LTA$_4$ hydrolase full-length cDNA clone (NM_000895) was purchased from OriGene Technologies (Rockville, Md.). The gene was amplified by polymerase chain reaction and transferred via pDONR201 into the bacterial expression vector pDEST17 by recombination (both plasmids from Invitrogen, Carlsbad, Calif.). The resulting construct was transformed into *Escherichia coli* BL21-AI (Invitrogen), and expression was induced by chemical induction with arabinose. The recombinant enzyme was purified by chromatography on a FPLC system (Amersham Biosciences, Uppsala, Sweden) using immobilized metal affinity chromatography (Ni-NTA Superflow, Qiagen, Hilden, Germany) and anion exchange chromatography (MonoQ HR 10/10, Amersham Biosciences).

The compounds of the invention were incubated in a series of dilutions with 200 nM of recombinant enzyme in assay buffer (100 mM Tris-HCl, 100 mM NaCl, 5 mg/ml fatty-acid free BSA, 10% DMSO, pH 8.0) for 10 min at room temperature to allow binding between LTA$_4$ hydrolase and the inhibitors. LTA$_4$ was prepared by alkaline hydrolysis of LTA$_4$ methyl ester (Biomol, Plymouth Meeting, Pa., or Cayman Chemicals, Ann Arbor, Mich.). A solution of 10 µg of the ester was dried under a nitrogen stream and redissolved in 60 µl of a solution of 80% aceton and 20% 0.25 M NaOH. After incubation for 40 min at room temperature the resulting approximately 500 µM tock of LTA$_4$ was kept at −80° C. for no more than a few days prior to use.

Immediately before the assay, LTA$_4$ was diluted to a concentration of 10 µM in assay buffer (without DMSO) and added to the reaction mixture to a final concentration of 2 µM to initiate the enzyme reaction. After incubation for 120 sec at room temperature, the reaction was stopped by adding 2 volumes of chilled quenching buffer, containing acetonitril with 1% acetic acid and 225 nM LTB$_4$-d$_4$ (Biomol). The samples were then kept at 4° C. over night to complete protein precipitation and centrifuged for 15 min at 1800 g. LTB$_4$ formed was measured by LC-MS/MS using LTB$_4$-d$_4$ as an internal standard and an external LTB$_4$ standard (Biomol) as reference. Briefly, the analyte was separated from LTB$_4$ isomers formed by spontaneous hydrolysis of LTA$_4$ using isocratic elution (modified protocol from Mueller et al. (1996), J. Biol. Chem. 271, 24345-24348) on a HPLC system (Waters, Milford, Mass.) and analyzed on a tandem quadrupole mass spectrometer (Waters). MRM transitions followed on 2 channels were 335.2>195.3 (LTB$_4$) and 339.2>197.3 (LTB$_4$-d$_4$). Based on the amounts of LTB$_4$ found at each inhibitor concentration, a dose-response curve was fitted to the data and an IC$_{50}$ value was calculated.

| structure | example | IC50 (uM) |
|---|---|---|
| [structure 1] | 1 | B |
| [structure 2] | 2 | A |
| [structure 3] | 3 | A |

-continued

| structure | example | IC50 (uM) |
|---|---|---|
| 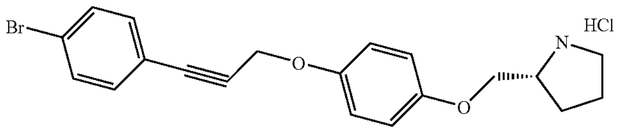 | 4 | B |
| 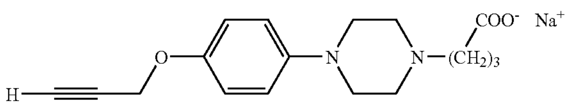 | 5 | B |
| 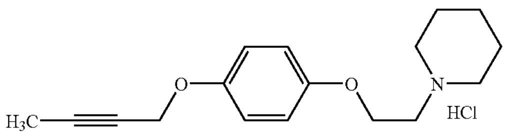 | 6 | B |

A = <5 uM,
B = 5-20 uM,
C = 20-30 uM

We claim:

1. A compound of the formula:

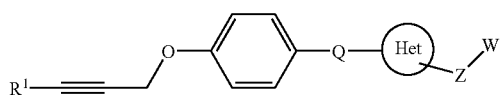

wherein
R$^1$ is selected from the group consisting of H, alkyl, aryl, heteroaryl, aryl substituted with from one to three substituents independently selected from the group consisting of halogen, loweralkyl, loweracyl, loweralkoxy, fluoroloweralkyl, fluoroloweralkoxy, hydroxyloweralkyl, formyl, cyano, and nitro; and
heteroaryl substituted with from one to three substituents independently selected from the group consisting of halogen, loweralkyl, loweracyl, loweralkoxy, fluoroloweralkyl, fluoroloweralkoxy, formyl, cyano, and nitro;
Het is pyrrolidine;
Q is (CH$_2$)$_{1-8}$; in which one or two (CH$_2$) may optionally be replaced by —O—, —NR$^1$—, —SO—, —S(O)$_2$—, —C(=O)— or —C=O(NH)—, provided that said —O—, —NR$^1$—, —SO—, —S(O)$_2$—, —C(=O)— or —C=O(NH)— are separated by at least one —(CH$_2$)—; and when the pyrrolidine nitrogen is the point of attachment to the parent structure, Q may additionally be a direct bond;
Z is (CH$_2$)$_{1-10}$; in which one or two (CH$_2$) may optionally be replaced by —O—, —NR$^1$—, —SO—, —S(O)$_2$—, —C(=O)— or —C=O(NH)—, provided that said —O—, —NR$^1$—, —SO—, —S(O)$_2$—, —C(O)— or —C=O(NH)— are not at the point of attachment to nitrogen and are separated by at least one —(CH$_2$)—;
W is selected from acyl, hydroxyl, carboxyl, amino, carboxamido, aminoacyl, —COOalkyl, —CHO, sulfonamide, —C(O)fluoroalkyl, —C(O)CH$_2$C(O)Oalkyl, —C(O)CH$_2$C(O)Ofluoroalkyl, —SH, —C(O)NH(OH), —C(O)N(OH)R$^4$, —N(OH)C(O)OH, —N(OH)C(O)R$^4$, heterocyclyl, substituted aryl, and substituted heterocyclyl, or
taken together ZW are H or —COOalkyl; and
R$^4$ is selected from the group consisting of H and lower alkyl.

2. A compound according to claim 1 of formula

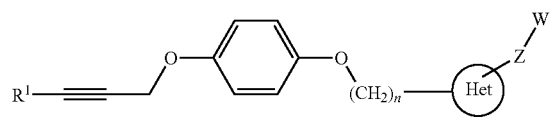

wherein n is 1-4.

3. A compound according to claim 2 wherein ZW is H, —COOalkyl or
Z is (CH$_2$)$_{1-5}$ and
W is COOH.

4. A compound according to claim 3 wherein R$^1$ is chosen from H, methyl, phenyl and substituted phenyl.

5. A pharmaceutical composition comprising a pharmaceutically acceptable carrier and a therapeutically effective amount of at least one compound according to claim 1.

* * * * *